United States Patent
Alleyne

(10) Patent No.: US 8,591,537 B2
(45) Date of Patent: Nov. 26, 2013

(54) SURGICAL APPRATUS FOR CUTTING TISSUE

(75) Inventor: Cargill H. Alleyne, Martinez, GA (US)

(73) Assignee: Medical College of Georgia Research Institute, Inc., Augusta, GA (US)

( * ) Notice: Subject to any disclaimer, the term of this patent is extended or adjusted under 35 U.S.C. 154(b) by 937 days.

(21) Appl. No.: 12/174,463

(22) Filed: Jul. 16, 2008

(65) Prior Publication Data

US 2009/0043323 A1 Feb. 12, 2009

Related U.S. Application Data

(60) Provisional application No. 60/959,850, filed on Jul. 17, 2007.

(51) Int. Cl.
*A61B 17/3201* (2006.01)

(52) U.S. Cl.
USPC .......................................... 606/174; 606/190

(58) Field of Classification Search
USPC ........... 606/167, 174, 190, 198, 201, 205, 45, 606/51, 52; 600/201, 210, 214, 215, 235
See application file for complete search history.

(56) References Cited

U.S. PATENT DOCUMENTS

| | | | | |
|---|---|---|---|---|
| 4,243,047 A | * | 1/1981 | Olsen | 600/564 |
| 5,458,598 A | * | 10/1995 | Feinberg et al. | 606/52 |
| 6,773,434 B2 | * | 8/2004 | Ciarrocca | 606/51 |
| 7,695,470 B1 | * | 4/2010 | Stewart et al. | 606/51 |

* cited by examiner

*Primary Examiner* — Kathleen Holwerda
*Assistant Examiner* — Sarah W Aleman
(74) *Attorney, Agent, or Firm* — Gardner Groff Greenwald & Villanueva, P.C.

(57) ABSTRACT

A system of separating a membrane from underlying tissue. The system includes a separation member operable to separate the membrane from the tissue and a cutting element in communication with the separation member. The cutting element is also operable to dissect the membrane without harming the underlying tissue.

12 Claims, 18 Drawing Sheets

SURGICAL APPRATUS FOR CUTTING TISSUE

CROSS-REFERENCE TO RELATED APPLICATION

This application claims the benefit of U.S. Provisional Patent Application Ser. No. 60/959,850 filed Jul. 17, 2007, which application is incorporated herein by reference in its entirety for all purposes.

TECHNICAL FIELD

The present invention relates generally to the field of surgical instruments, and more particularly, to surgical instruments specializing in the separation and cutting of tissue.

BACKGROUND OF THE INVENTION

There are many situations when a surgeon must cut into delicate tissue or membranes when operating on a patient, while at the same time, the surgeon must protect surrounding tissue from being damaged. One such example is when a surgeon is performing a craniotomy. During a craniotomy to access a patient's brain, a surgeon must first remove a piece of the patient's cranium to expose the dura (or dural membrane), which lines and encapsulates the brain of the patient. One or more incisions must then be made in the dura by the surgeon to reveal the patient's brain. However, because the dura is often tightly secured against the patient's brain, a surgeon must very carefully incise the dura, so as not to damage the delicate brain tissue just below.

Presently, this is accomplished though the use of several tools. First, a knife is used to create a tiny opening in the dura. Then, the surgeon uses a pair of forceps, or other type of tool, to hold open an edge of the opening in the dura. With the surgeon's other hand, a pair of scissors or other cutting implement is used to cut open the dura. In order to protect the brain from incidental damage caused by the cutting implement, a pad is placed into the opening between the dura and brain to prevent the cutting implement from penetrating brain tissue. It can be very difficult to accurately place the pad in the proper location to minimize incidental damage to the brain. Following each cut along the dura, the surgeon must reposition both the forceps and the protective pad before making an additional cut with the cutting implement. This process wastes precious time and is a very difficult maneuver for the surgeon to accomplish. Furthermore, the current method for safely removing dura requires that both hands of the surgeon be actively engaged at all times.

Other types of surgeries similarly require the skillful cutting of tissue or membranes, such that underlying tissue is unharmed. Therefore, it can be seen that a need exists for a surgical apparatus that provides a safe and simplified method of cutting tissue, while preserving underlying tissue. Additionally, needs exist for a surgical apparatus that saves surgical time and can be substantially utilized with one hand. It is to the provision of these needs and others that the present invention is primarily directed.

SUMMARY OF THE INVENTION

The present invention relates to system of separating a membrane from underlying tissue. The system includes a separation member operable to separate the membrane from the tissue and a cutting element in communication with the separation member. The cutting element is also operable to dissect the membrane without harming the underlying tissue. The present invention is advantageous because it allows a user to separate and dissect adjacent layers of tissue with one hand. Additionally, the present invention permits safe and reliable separation and dissection of delicate tissue layers.

In one aspect, the present invention relates to a surgical apparatus. The surgical apparatus includes a cutting element and a separation element in operable communication with the cutting element. The apparatus also includes a stationary post coupled to the separation member and a mobile post mechanically linked to the cutting element. Additionally, the apparatus includes a first handle coupled to the stationary post and a second handle mechanically linked to the mobile post. User manipulation of the second handle operates the cutting element.

In another aspect, the invention relates to a surgical system for separating a first layer of tissue from a second layer of tissue. The system includes a first separation member operable to be inserted between the first layer of tissue and the second layer of tissue. The first separation member is further operable to spread apart the first and second layers of tissue. The system also includes a second separation member in sliding engagement with the first separation member. The second separation member is operable to tighten the first layer of tissue against the first separation member. Additionally, the system includes a cutting element in operable communication with the first separation member and the cutting element is also operable to cut the first layer of tissue.

In another aspect, the invention relates to a surgical tool to separate and cut a membrane from underlying tissue. The tool includes a first separation member operable to be placed between the membrane and the underlying tissue and is further operable to lift the membrane from the underlying tissue. The tool also includes a second separation member operable to hold the membrane against the first separation member. Finally, the tool includes at least one cutting element rotatably coupled to the first separation member operable to cut the membrane.

In still another aspect, the invention relates to a method of separating and dissecting a top layer of tissue from an underlying layer of tissue. The method includes the first step of making an incision in the top layer of the tissue. Next, the method includes operating a surgical apparatus to separate the top layer of tissue from the underlying layer of tissue. Then, the method includes the step of operating the surgical apparatus to dissect the top layer of tissue. The surgical apparatus includes a separation member operable to separate the top layer of tissue from the underlying layer of tissue and a cutting element in communication with the separation member. The cutting element is operable to dissect the top layer of tissue.

These and other aspects, features, and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

DETAILED DESCRIPTION OF EXAMPLE EMBODIMENTS

Figure 1:
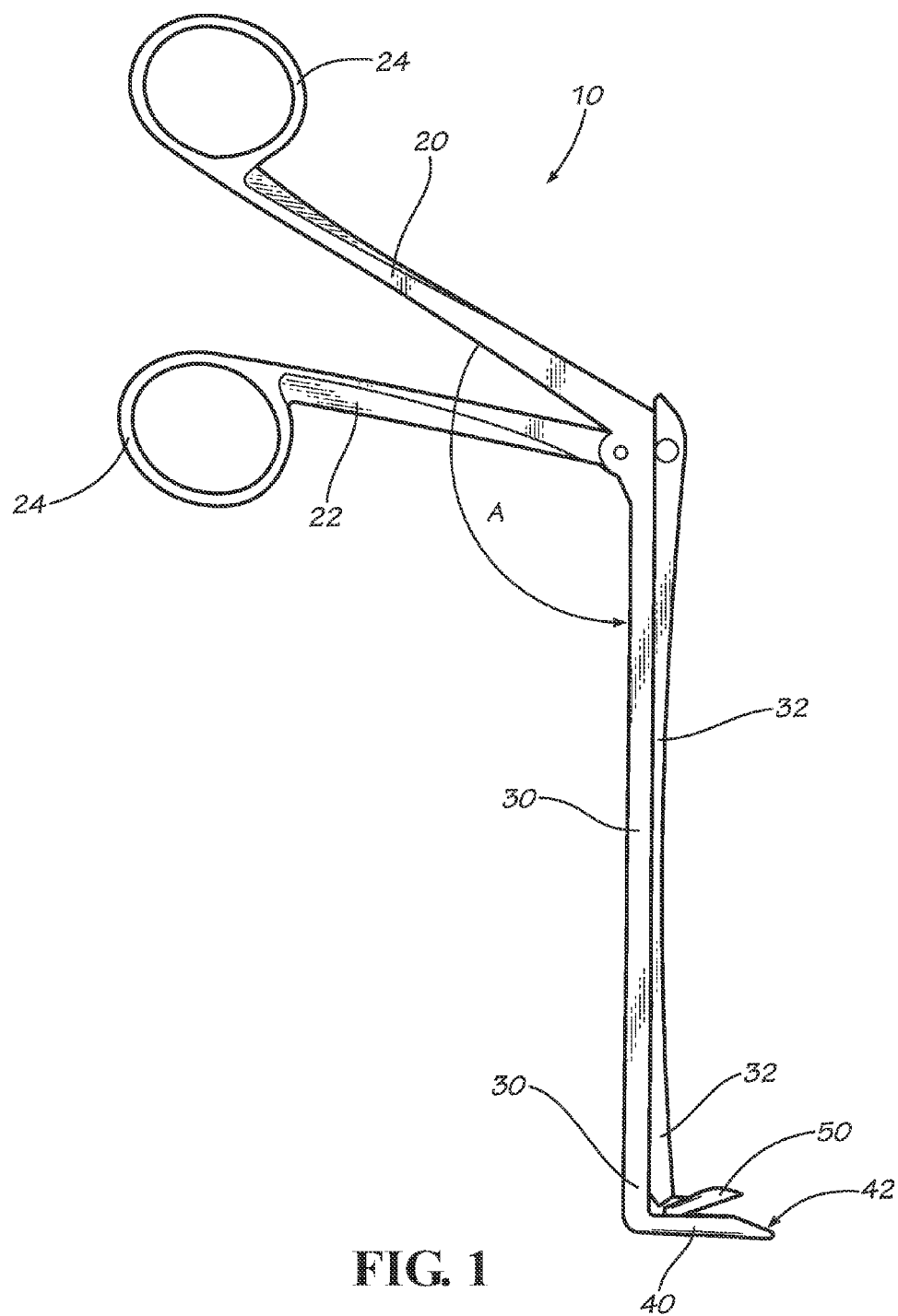
FIG. 1 is a side view of an example embodiment of a surgical cutting tool according to a first form of the present invention.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, FIGS. 1-18 depict several surgical apparatuses according to example embodiments of the present invention. Generally, the surgical apparatuses of the present invention can be used by a surgeon to separate a first layer of tissue from a second layer of tissue. The surgical apparatuses then allow a surgeon to cut or dissect the first layer of tissue, while preventing damage from occurring to the second layer of tissue, such that the second layer of tissue is largely preserved. While the present invention is discussed herein as being applicable to separate and dissect the dural membrane from a patient's underlying brain tissue, nothing herein is intended to limit the present invention to such applications. In fact, the present invention can be applied during various other surgical procedures, including, but not limited to, spinal surgeries, abdominal surgeries, and thoracic surgeries. However, it has been found that the present invention is particularly useful during brain operations, and specifically in removing a patient's dural membrane to expose brain tissue, as is it very important not to harm any brain tissue when removing the dural membrane.

With particular reference now to depicted example embodiments of the present invention, FIG. 1 shows a surgical cutting tool 10 according to a first form of the invention. The cutting tool 10 generally includes first and second handles 20, 22, a stationary post 30, a mobile post 32, a first separation member 40, and a cutting element 50. In example embodiments, generally the cutting tool 10 is formed from stainless steel, although in other example embodiments, the cutting tool can be formed from plastic, steel, titanium, aluminum, biocompatible materials, rubber, and/or a combination of the same. The cutting tool 10 can range widely in size, as will be discussed herein, depending on the particular application the cutting tool 10 of the present invention is intended for.

The handles 20, 22 are generally scissor-like as depicted in FIG. 1, wherein each handle has at least one finger ring or hold 24 at a distal end thereof. The handles 20, 22 are rotatably coupled together at the proximal ends thereof about a pivot point, such that the handles can be manipulated towards and away from each other as with traditional scissors. The finger rings 24 allow the user to firmly grip the cutting tool 10 and manipulate each handle 20, 22 with a single finger. The first handle 20 is coupled to the stationary post 30 and the second handle 22 is mechanically linked to the mobile post 32. As the second handle 22 is moved away from the first handle 20, the mobile post 32 is vertically levered upwards. Conversely, as the second handle 22 is moved towards the first handle 20, the mobile post 32 is vertically lowered.

The mobile post 32 and the stationary post 30 are depicted in FIG. 1 as being in sliding engagement, however, in alternate example embodiments, the posts can be spaced apart from each other as desired. The stationary post 30 is coupled to the separation member 40 and the mobile post 32 is mechanically linked to the cutting element 50. In depicted example embodiments, the mobile post 32 and stationary post 30 are narrow elongate rods and can vary between about 2 inches in length to about 18 inches in length. Preferably, the mobile post 32 and stationary post 30 are between about 4 inches in length to about 8 inches in length. In alternate embodiments, the dimensions of the mobile post 32 and stationary post 30 can vary as desired. In depicted embodiments, the angle A between the first handle 20 and the stationary post 30 is about 120 degrees. In alternate embodiments, the angle A can be between about 90 degrees and about 180 degrees as desired.

Figure 2:
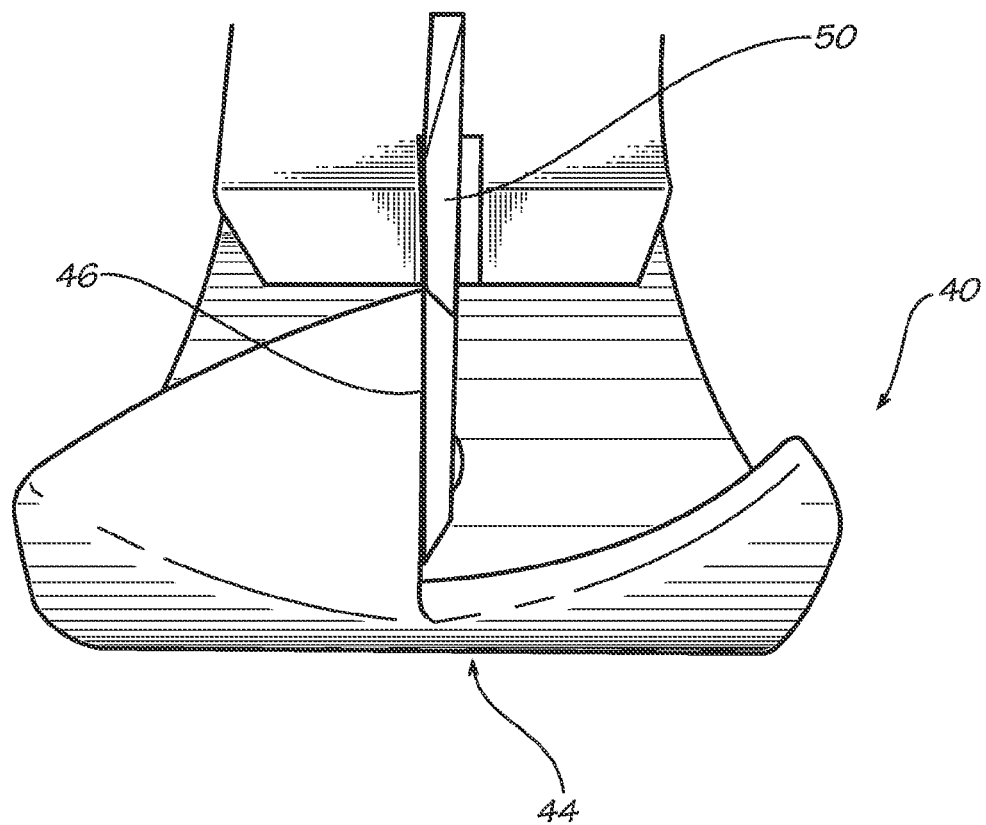
FIG. 2 is a close-up front view of the separation member and cutting element of FIG. 1.
Figure 3:
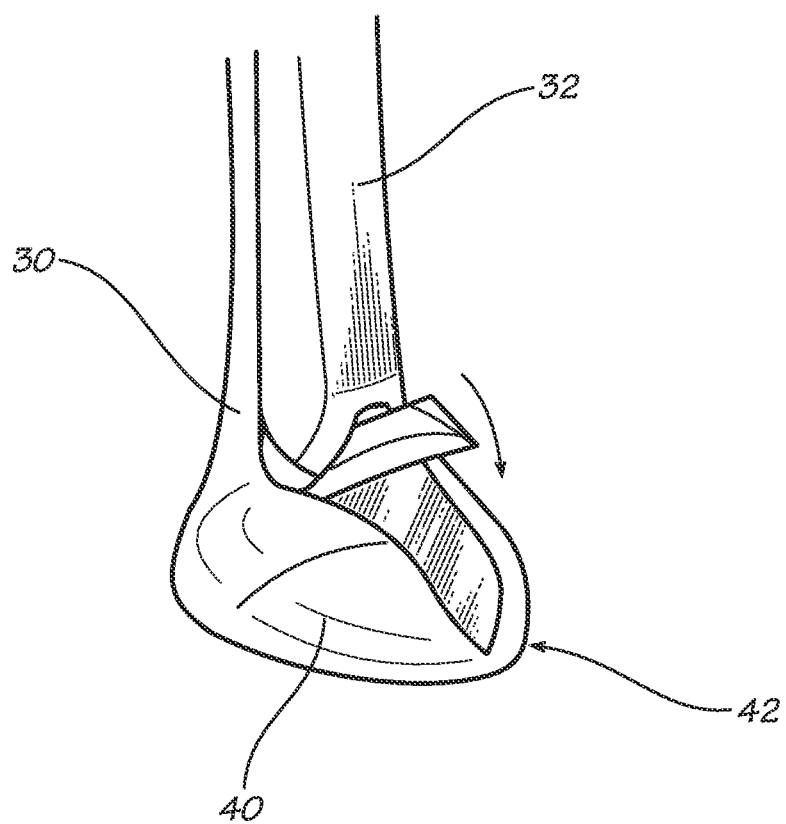
FIG. 3 is a close-up perspective view of the separation member and cutting element of FIG. 1, showing the cutting element in the open position.
Figure 4:
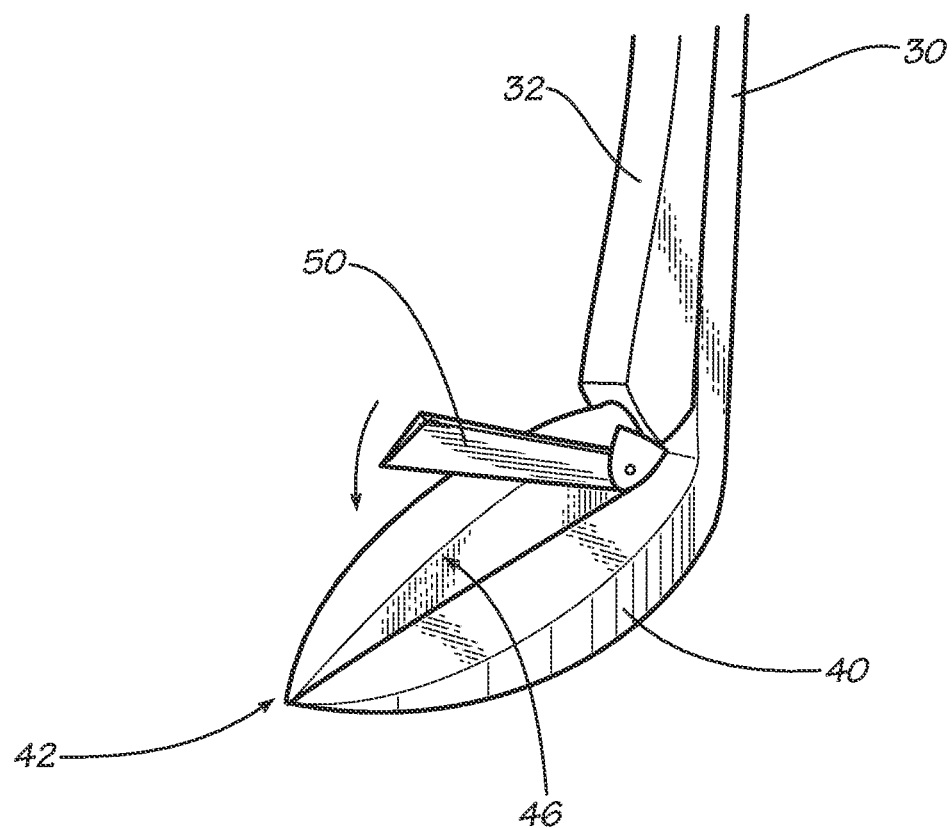
FIG. 4 is a close-up perspective view of the separation member and cutting element of FIG. 1, showing the cutting element in the open position.

The separation member 40, which is shown in more detail in FIGS. 2-4, generally includes an angled tip 42 to allow a user to wedge the tip in between successive layers of tissue. The angled tip 42 is thus operable to create a gap between two layers of tissue. As it can be seen in FIGS. 2-4, the separation member 40 includes a smooth bottom surface 44, and generally rounded edges, to protect the underlying tissue from being damaged by the separation member as it is inserted between two layers of tissue. In particular, the smooth bottom surface 44 protects the underlying tissue from abrasion damage, punctures, and prevents the cutting element 50 from engaging the same. In the example embodiments shown in FIGS. 1-4, the separation member 40 also includes a fixed surface 46 that is perpendicular to the bottom surface 44 of the member 40 for cooperating with the cutting element 50 to provide a cutting surface.

In example embodiments, the cutting element 50 is a single blade that is in mechanical communication with the mobile post 32. The cutting element 50 can be connected to the mobile post 32 with a rotating joint, hinge, or other suitable connectors. The cutting element 50 moves from a closed/down position when the mobile post 32 is lowered, to a open/up position when the mobile post is raised. It is preferable that the cutting element 50 be biased, such as with a spring, and more preferable that the cutting element be biased in the closed/down position to avoid unwanted damage to tissue. However, in alternate embodiments, the cutting element 50 is neutral or biased in the open/up position as desired. The cutting element 50 is preferably formed from stainless steel, although in alternate embodiments, the cutting element is formed from rubber, plastic, or other metals. The cutting element 50 can be removable, such that the blade can be sharpened as desired, or the cutting element can be replaced (such as one-time-use blade or disposable blade).

The cutting tool 10 of the present invention can safely and efficiently separate two adjacent layers of tissue, while permitting a user to cut only the overlying tissue. For example, when a surgeon operates on a patient's brain, the surgeon must separate the dural membrane from the underlying brain tissue. In operation, a user first utilizes a knife or other implement to create a tiny hole in the overlying dural membrane. Once the hole in the membrane is established, the user inserts the angled tip 42 of the separation member 40 into the hole and slides the smooth bottom surface 44 of the separation member along the underlying brain tissue to form a gap between the brain tissue and the overlying dural membrane. As the user begins to slide the separation member 40 into the hole, the user moves the second handle 22 away from the first handle 20 to manipulate the cutting element into the open/up position. As the separation member 40 slides between the dural membrane and the underlying brain tissue, the user can open and close the cutting element 50 against the cooperating surface 46 of the separation member to cut the dural membrane by manipulating the handles 20, 22 as desired. Because the cutting element 50 is prohibited from engaging the underlying brain tissue, the brain tissue is protected from unwanted damage. While the cutting tool 10 can be used for various other tissue dissections, the tool's advantages can readily be seen in the above described procedure due to the extreme importance of protecting brain tissue from unwanted damage. An advantage to the surgical tool 10 is that the user can operate it with substantially one hand, leaving the other hand free for other uses.

Figure 5:
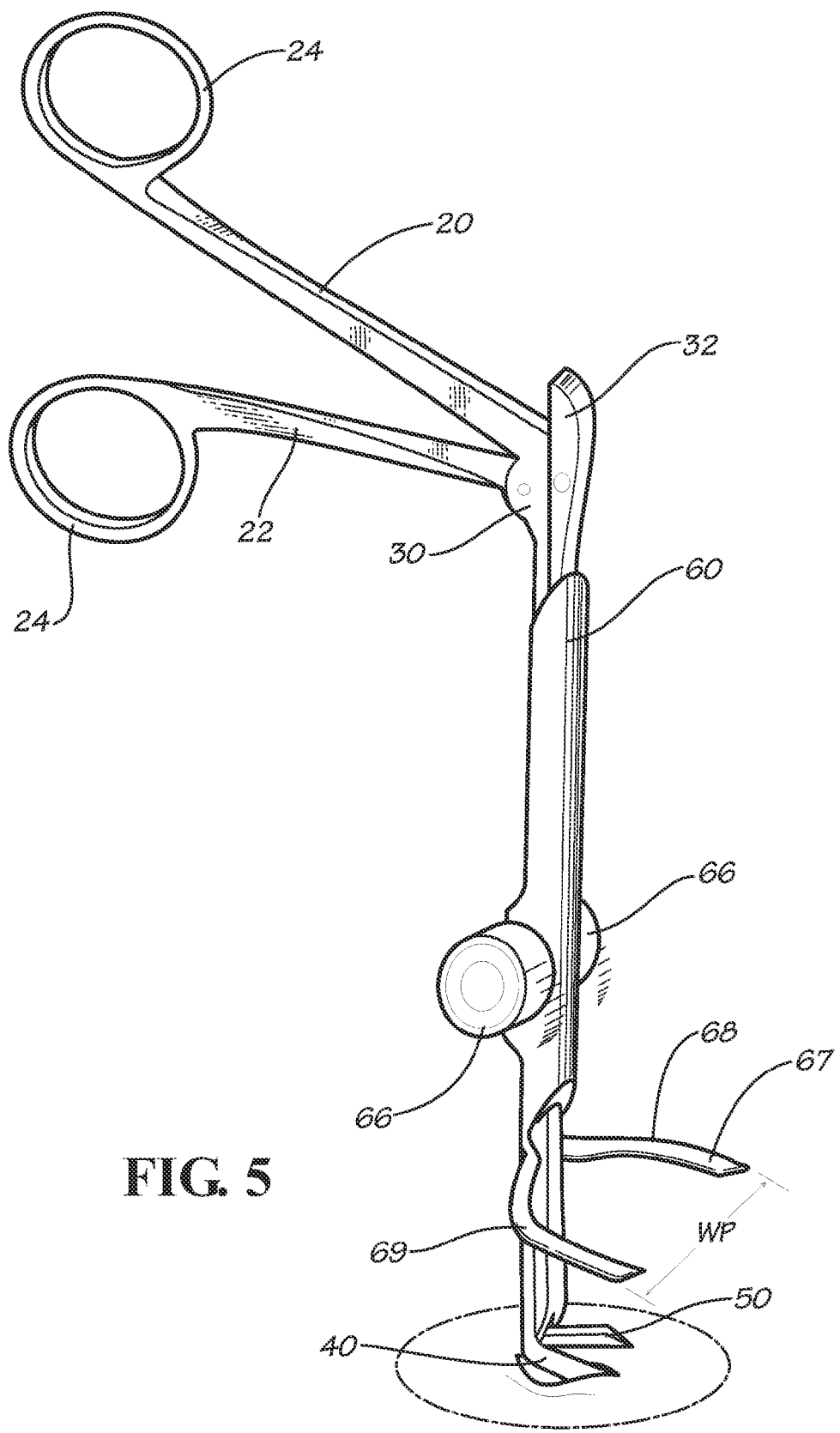
FIG. 5 is a perspective view of the surgical cutting tool of FIG. 1, shown with a second separation member.
Figure 6:
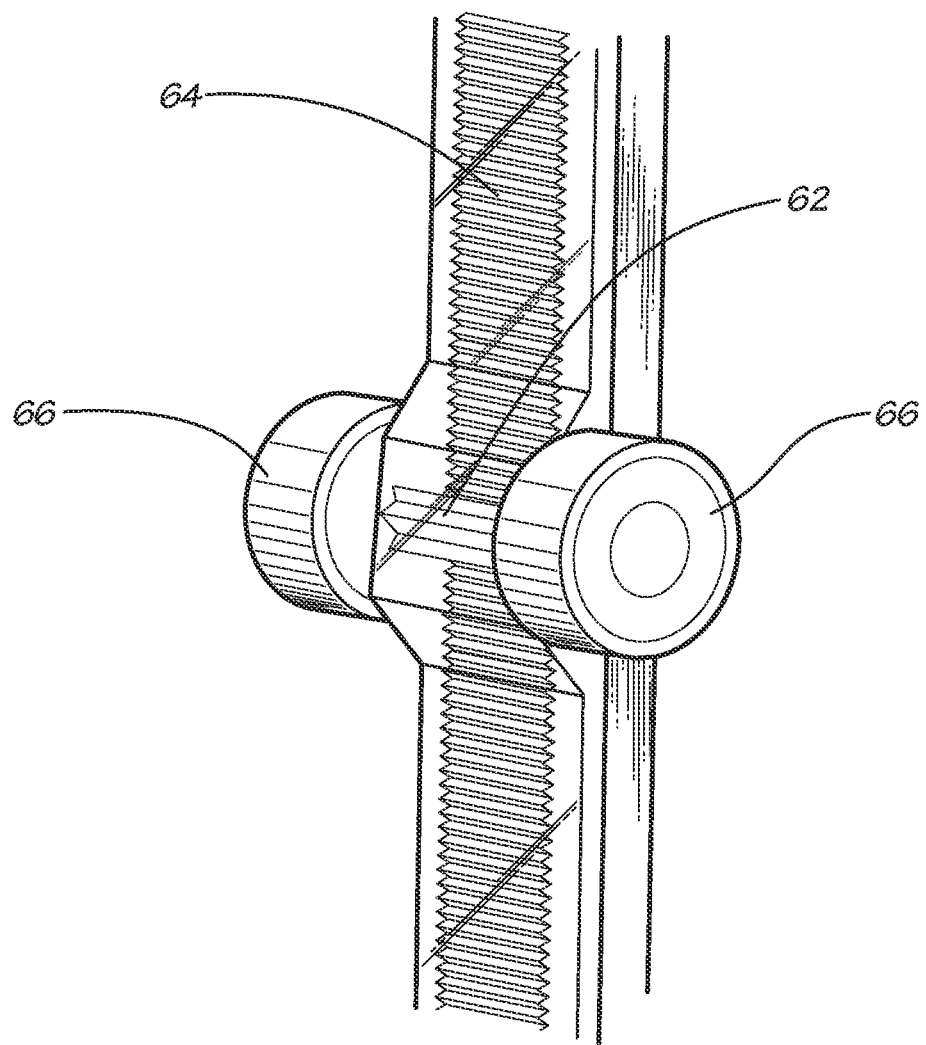
FIG. 6 is a close-up perspective view of the surgical cutting tool of FIG. 5, showing an example attachment mechanism of the second separation member.
Figure 7:
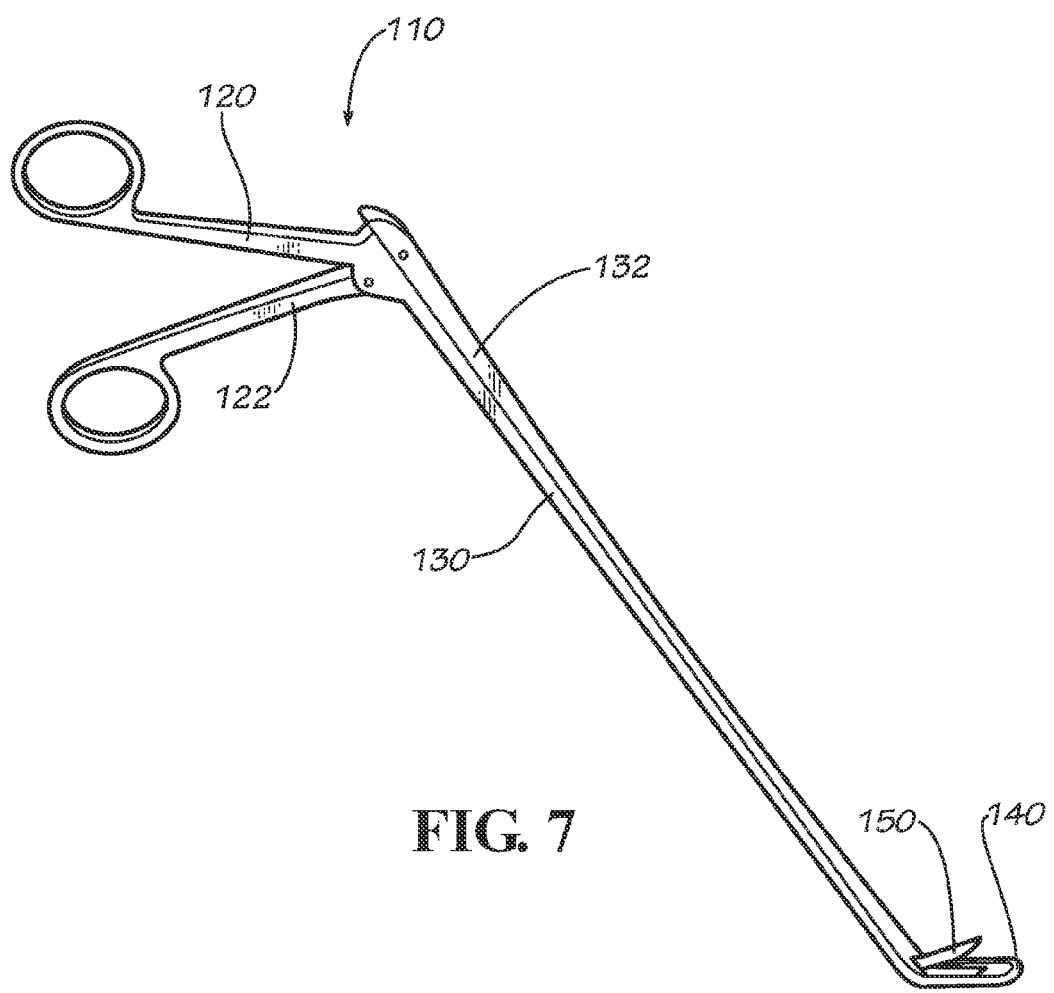
FIG. 7 is a perspective view of an example embodiment of a surgical cutting tool according to a second form of the present invention.

As shown in FIGS. 5-6 the surgical tool 10 can further include a second separation member 60 to help facilitate the separation of two adjacent tissue layers. In example embodiments, the second separation member 60 is movably coupled to the stationary post 30, as shown in the drawing figures. As depicted in FIG. 6, the second separation member 60 can be coupled to the stationary post 30 with an adjustable pinion gear 62 that is received by a corresponding rack 64 in the stationary post 30. In example embodiments, one or more rotatable handles 66 are coupled to the pinion gear 62 for adjusting the position of the second separation member 60 along the rack 64. In alternate embodiments, the second separation member 60 can be slidably coupled to the stationary post 30 or otherwise movably connected thereto as desired. The distal end of the second separation member 60 includes a pressure plate 67, which further includes a first arm 68 and a second arm 69. The width WP between the first arm 68 and second arm 69 can vary as desired, however, it is preferable that the width WP be greater than the corresponding width of the separation member 40. In alternate embodiments, the pressure plate can include only one arm, more than two arms, a ring, or otherwise as desired. To aid the surgical tool 10 in separating two adjacent layers of tissue, such as, but not limited to, the dural membrane from underlying brain tissue, the pressure plate 67 can be lowered along the stationary post 30 to apply pressure to the dural membrane. As the pressure plate 67 is lowered to the surface of the dural membrane (or other overlying tissue), the dural membrane between the first arm 68 and second arm 69 is tightened over the top of the first separation member 40, creating a "tent-like" effect. This tightening of the dural membrane facilitates further separation of the tissue layers and allows a user to make crisper cuts along the dural membrane, which results in less damage to the dural tissue.

FIGS. 7-10 depict example embodiments of a surgical tool 110 according to a second form of the present invention. Surgical tool 110 is similar to the first form of the present invention, and generally includes first and second handles 120, 122, a stationary post 130, a mobile post 132, a first separation member 140, and a cutting element 150.

Figure 8:
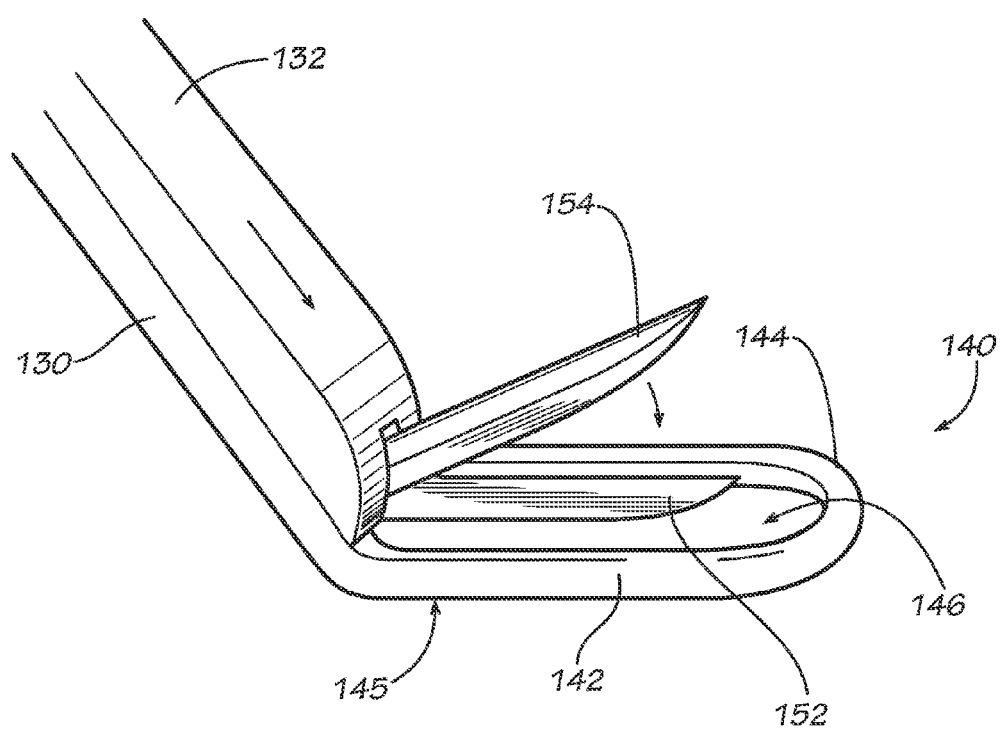
FIG. 8 is a close-up perspective view of the surgical cutting tool of FIG. 7, showing the separation member and cutting element in detail.
Figure 9:
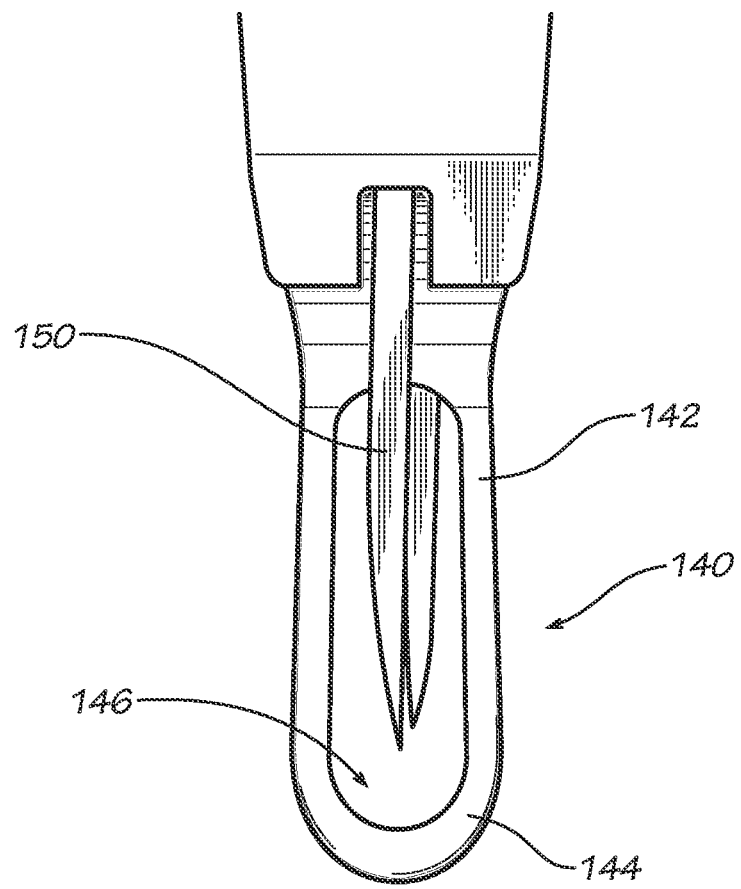
FIG. 9 is a close-up plan view of the surgical cutting tool of FIG. 7, showing the separation member and cutting element in detail.
Figure 10:
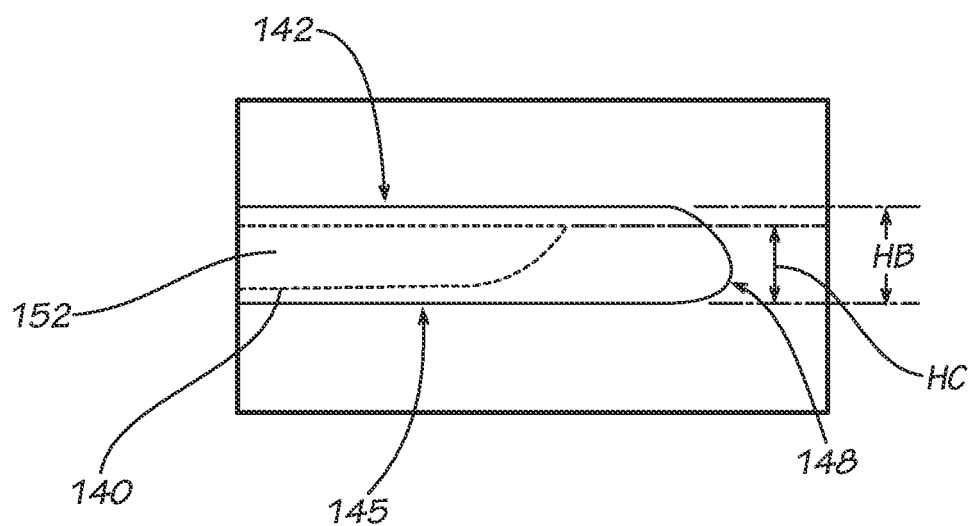
FIG. 10 is a close-up partial side view of the surgical cutting tool of FIG. 7, showing the separation member and cutting element in detail.

As better seen in FIGS. 8-9 the separation member 140 differs from the first form of the invention as it comprises a generally oval footplate 142 defined by an outer rim 144 having a flat bottom surface 145 and a generally oval cutout 146. The separation member 140 is rigidly coupled to the stationary post 130. In example embodiments, the tip 148 of the separation member 140 is rounded, so that that the tip does not damage tissue upon contact, as seen in FIG. 10. In alternate embodiments, the tip 148 can be angled or blunt as desired. Referring again to FIG. 8 the cutting element 150 includes a fixed lower blade 152 and a movable upper blade 154. In example embodiments, the fixed lower blade 152 is coupled to the separation member 140. In alternate embodiments, the fixed lower blade 152 is directly coupled to the stationary post 130. The upper movable blade 154 is mechanically linked to the mobile post 132, and is raised and lowered by the same. As seen in FIG. 10, the height HB of the footplate 142 is generally greater than or equal to the height HC of the lower blade 152, such that the lower blade can slide beneath an overlying tissue layer without inadvertently damaging it. In alternate embodiments, the separation member 140 further includes a smooth flat plate (not shown) that extends across the bottom of the footplate 142 to provide a barrier between an underlying tissue and the lower blade 152.

Figure 11:
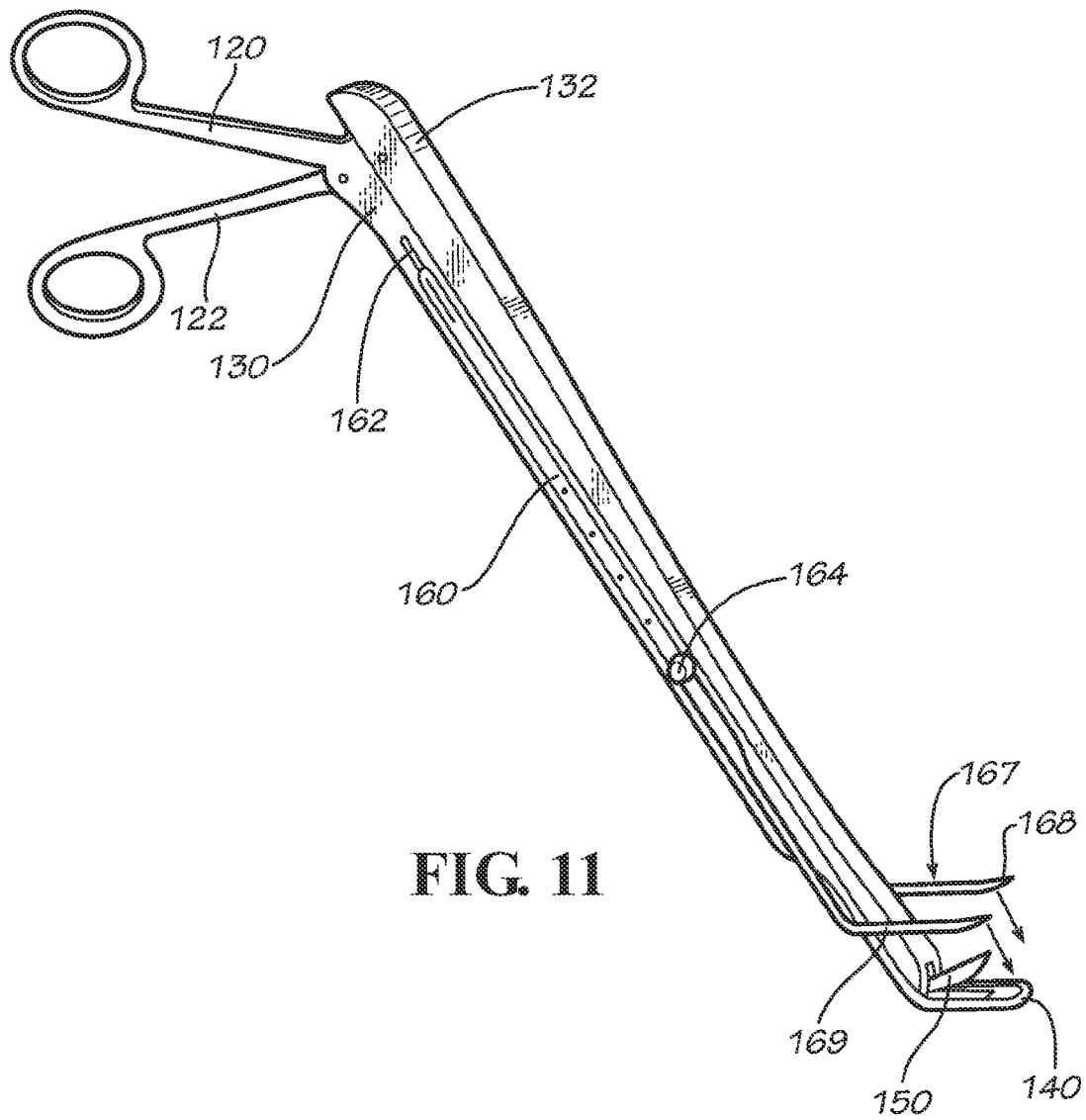
FIG. 11 is a perspective view of the surgical cutting tool of FIG. 7, shown with a second separation member.

Similar to the first form of the present invention, the second form of the invention can also be equipped with a second separation member 160, as depicted in FIG. 11. In this embodiment, the second separation member 160 can also be movably coupled to the stationary post 130. In depicted example embodiments, the second separation member 160 is shown slidably engaged within a cooperating recessed channel 162 in the stationary post 130. The second separation member 160 can be locked in place along the recessed channel 162 via a locking clip 164. In alternative embodiments, other conventional movable/slidable couplings can be employed as desired. In example embodiments, the second separation member also includes a pressure plate 167, which further includes a first arm 168 and a second arm 169. As described above when referencing the first form of the present invention, the pressure plate 167 in FIG. 11 can be lowered by a user to apply pressure to an overlying tissue, such as a dural membrane, to tighten a section of the same over the first separation member 140. This tightening aids the first separation member 140 in separating successive tissue layers and allows the overlying tissue layer to be cut with greater ease by the user.

Figure 12:
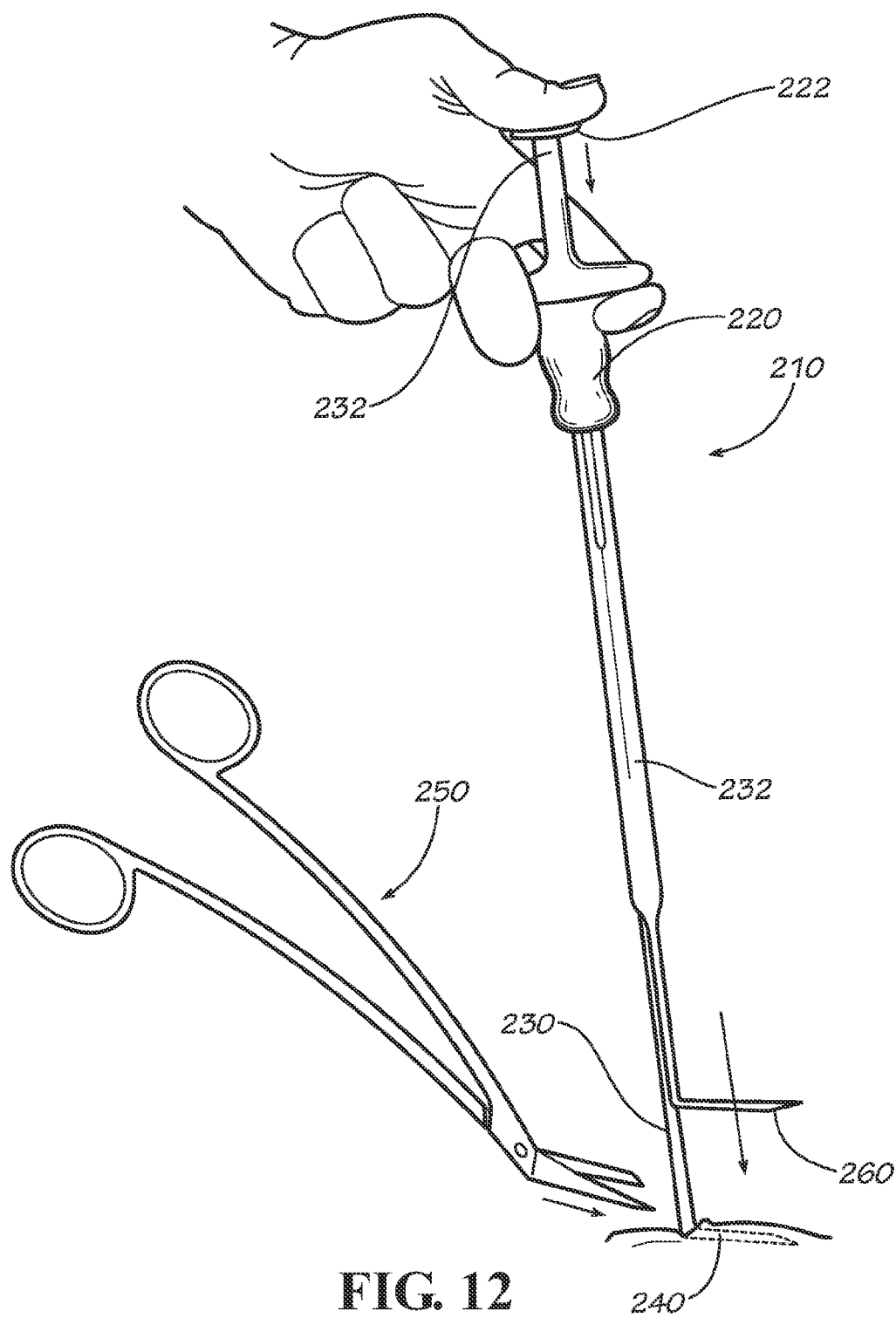
FIG. 12 is a perspective view of an example embodiment of a surgical tool system according to a third form of the present invention.
Figure 13:
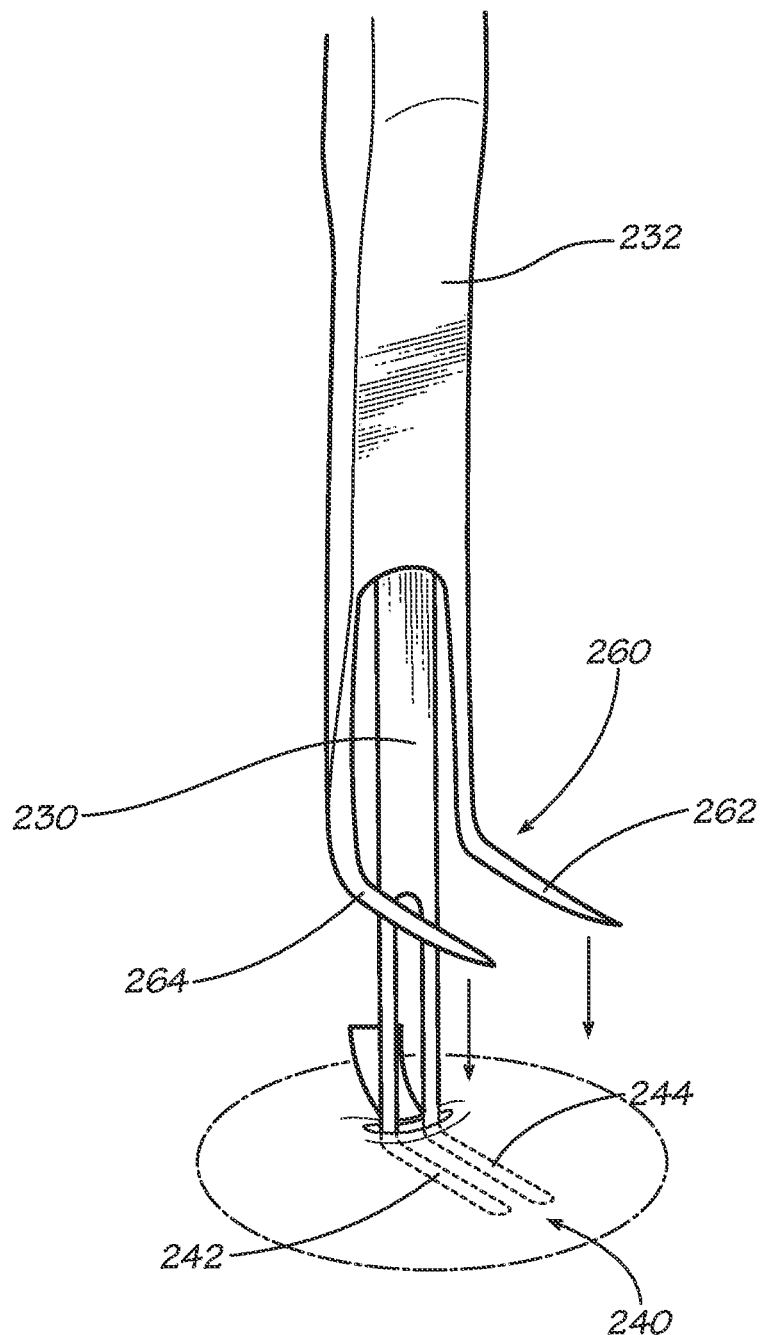
FIG. 13 is a close-up perspective view of the surgical tool system of FIG. 12, showing the second separation member in a raised position.
Figure 14:
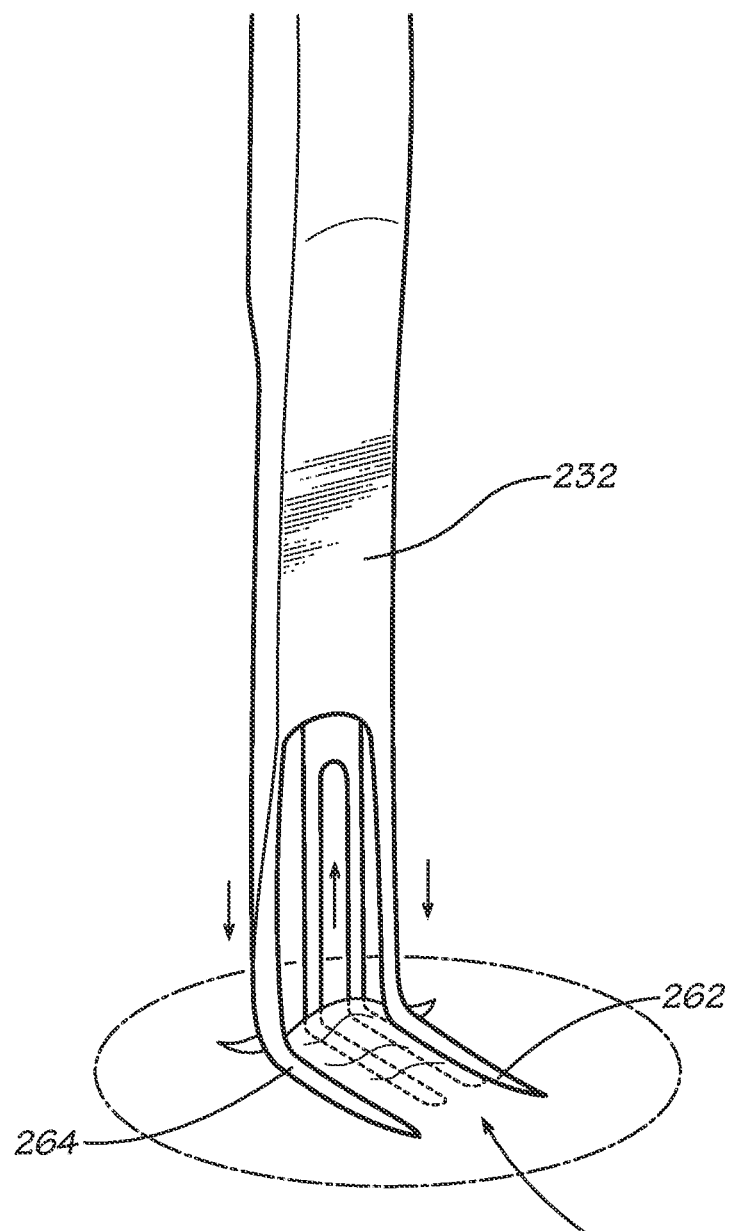
FIG. 14 is a close-up perspective view of the surgical tool system of FIG. 12, showing the second separation member in a lowered position.
Figure 15:
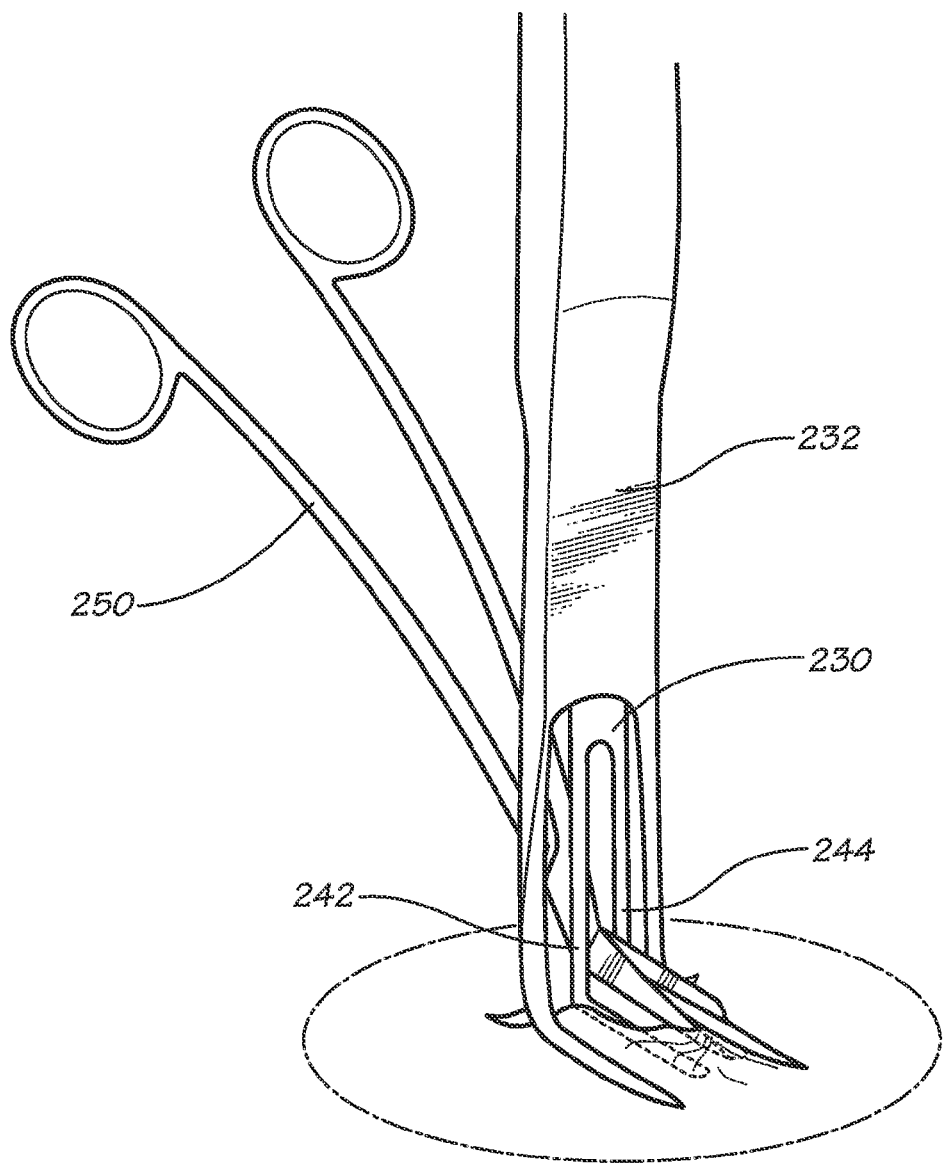
FIG. 15 is a close-up perspective view of the surgical tool system of FIG. 12, showing the first separation member, second separation member, and cutting implement in detail.

FIGS. 12-15 depict example embodiments of a surgical tool system 210 according to a third form of the present invention. Generally, the surgical tool 210 includes a first handle 220 coupled to a rigid fixed post 230, a second handle 222 coupled to movable post 232, a first separation member 240 coupled to the fixed post, a second separation member 260 coupled to the movable post, and a cutting implement 250 in operable communication with the first separation member (FIG. 15). In example embodiments, the movable post 232 and second handle 222 (or plunger) extend distally beyond the first handle 220. The movable post 232 is slidably coupled to the fixed post 230 and frictionally held in place. Alternatively, a ratchet or other conventional positional mechanism can be utilized to maintain the movable post's 232 position along the fixed post 230. As shown in FIG. 13, the first separation member 240 includes a first separating arm 242 and a second separating arm 244. In alternative embodiments, the separation member 240 can be a single arm. The second separation member 260 includes a first pressure arm 262 and a second pressure arm 264. Alternatively, one arm, more than two arms, or a pressure ring can be used.

Figure 16:
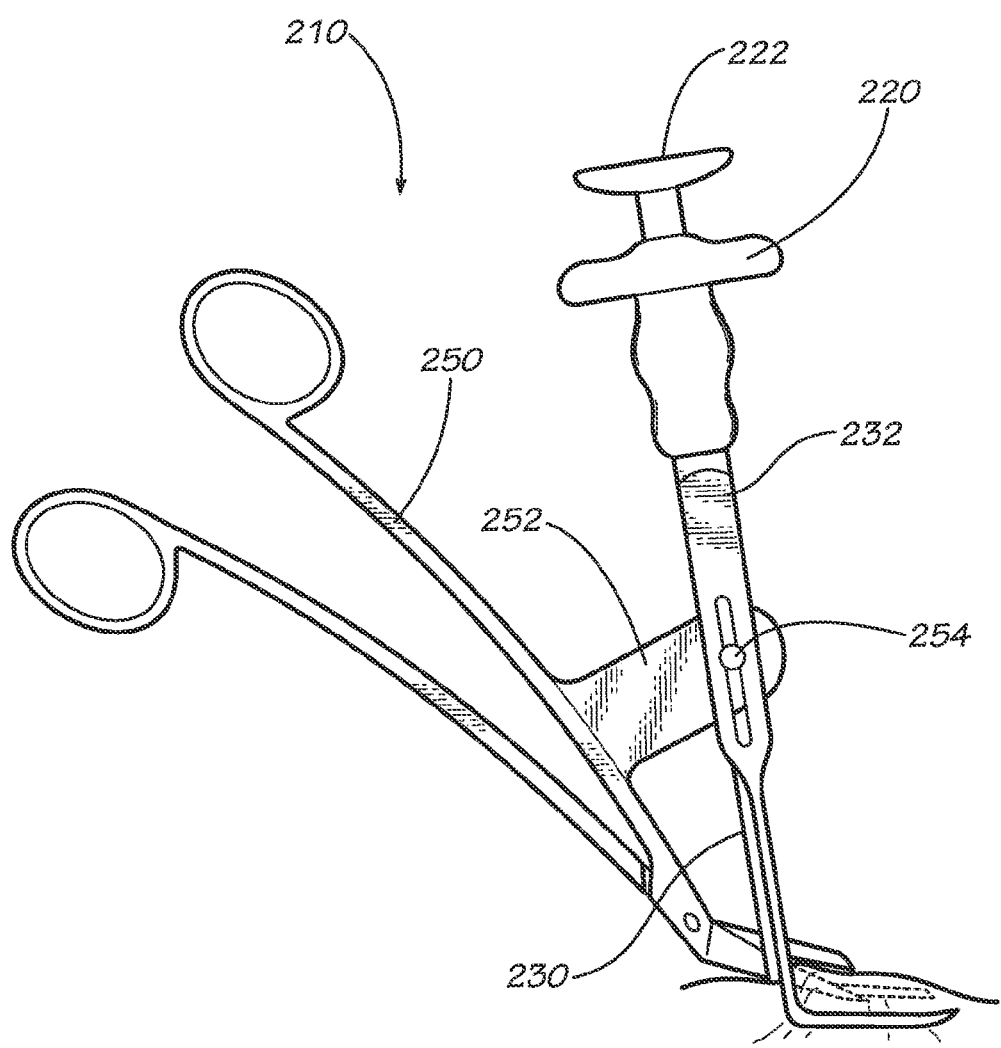
FIG. 16 is a side view of another example embodiment of a surgical tool system.

In operation, the surgical tool system 210 of the present invention can be used to separate and dissect the dural membrane from underlying brain tissue (or other adjacent layers of tissue) in a similar fashion as previously described forms of the present invention. First, a small hole or incision is made in the dural membrane with a knife or other cutting instrument. Next, the first separation member 240 is carefully inserted into the small hole. After the first separation member has been placed between the dural membrane and the underlying brain tissue, a user can lower the second separation member 260, as shown in FIGS. 12 & 14. To lower the second separation member 260 in example embodiments, a user can apply pressure to the second handle 222 and slide the movable post 232 towards the dural membrane. Once the second separation member 260 is applying pressure on the dural membrane, the user can pull up on the first handle 220/fixed post 230 to cause the dural membrane to be pulled tight over the first separation member 240 and further separate the dural membrane from the underlying brain tissue. Finally, a user can utilize a cutting implement 250 to cut the dural membrane, as depicted in FIG. 15. The user can use the gap between the first separating arm 242 and second separating arm 244 as a guide to direct the cutting implement 250. This process can be repeated for each successive tissue separation and cut. FIG. 16 depicts an alternate example embodiment, wherein the cutting implement 250 is rotatably coupled to the fixed post 230 via one or more coupling linkages 252. The coupling linkage 252 is hingedly connected to the fixed post 230 with a bearing, swivel, pin, or other conventional rotatable fastener 254.

Figure 17:
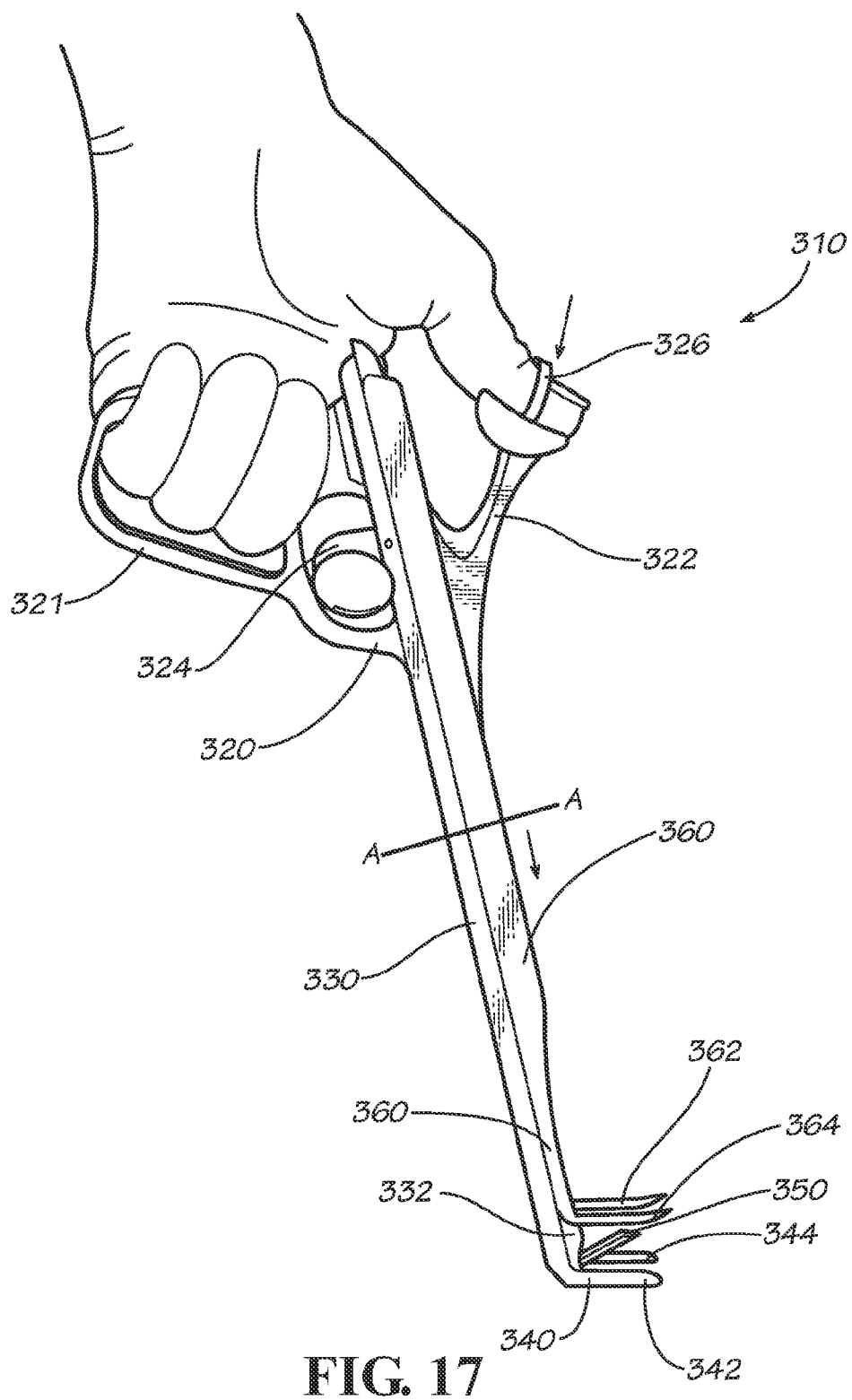
FIG. 17 is a perspective view of an example embodiment of a surgical cutting tool according to a fourth form of the present invention.
Figure 18:
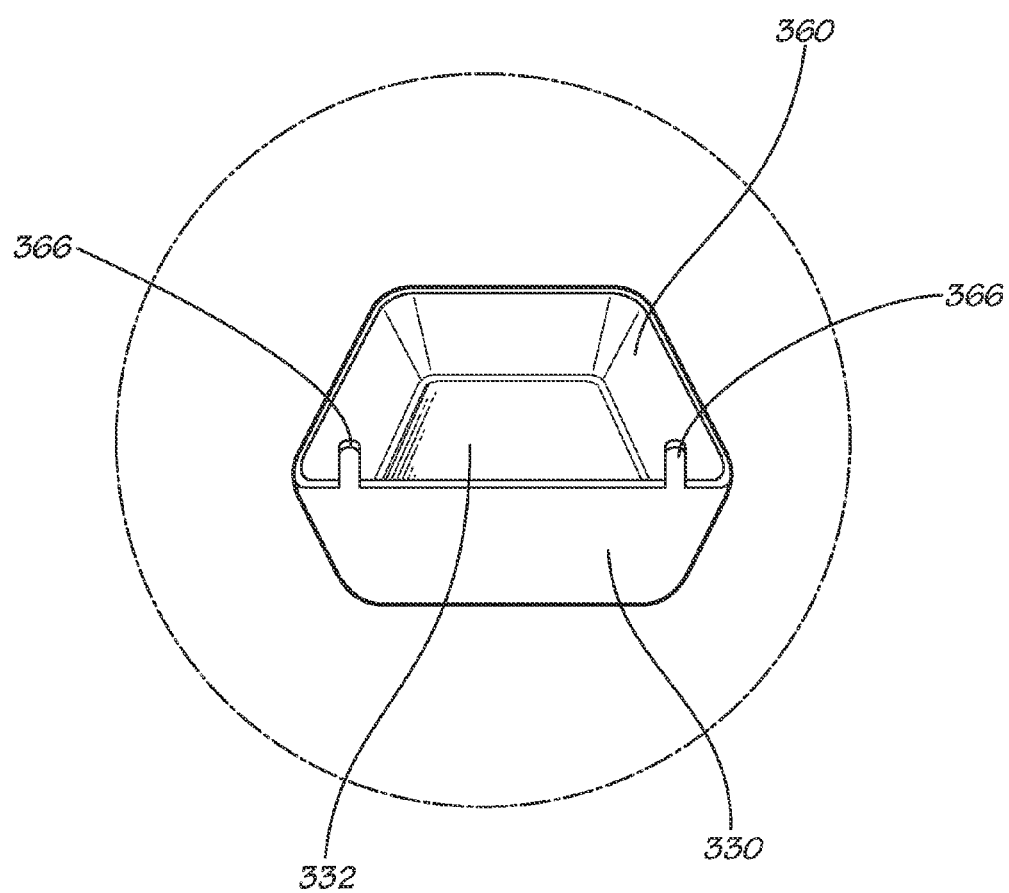
FIG. 18 is a cross-sectional view of the surgical cutting tool of FIG. 17 taken at line A-A.

In still another form of the present invention, a surgical cutting tool 310 is depicted in FIGS. 17-18, which operates similarly to the first and second forms of the present invention. In example embodiments, the cutting tool 310 generally includes a first handle 320, a second handle 322, a stationary post 330, a mobile post 332, a first separation member 340, a second separation member 360, and a cutting element 350. The first handle 320 includes a hand hold 321 and a trigger 324 to operate the mobile post 332 and the cutting element 350. In example embodiments, pulling the trigger 324 forces the mobile post 332 downward and closes the cutting element 350—such that the cutting element is in a cut position. The second handle 322 includes a finger ring/hold 326 to allow a user to grip the second handle with one finger. The second separation member 360 can be operated by applying pressure to the second handle 322 to either raise or lower the second separation member 360. The second separation member also includes a first pressure arm 362 and a second pressure arm 364. In example embodiments, the second separation member 360 includes recessed channels 366 that correspond with rails 334 in the stationary post 330 for allowing the second separation member to slide thereon. An example cross section of the surgical cutting tool 310 can be seen in FIG. 18. While the first separation member 340 is shown as including a pair of separation arms 342, 344, in alternative embodiments the first separation member 340 can be any of the separation members as described herein. In operation, the surgical tool 310 operates in a similar fashion as the other forms of the present invention, however, the surgical tool 310 provides a more comfortable grip for a user during operation.

While the invention has been described with reference to preferred and example embodiments, it will be understood by those skilled in the art that a variety of modifications, additions and deletions are within the scope of the invention, as defined by the following claims.

What is claimed is:

1. A surgical system for separating a dura membrane from underlying tissue and dissecting the dura membrane, comprising:
    a separation member operable to separate the dura membrane from the underlying tissue by being inserted between the dura membrane and the underlying tissue, wherein the separation member comprises a footplate in the form of an outer rim defining in internal cutout and a top surface and a bottom surface that together define a height that elevates the dura membrane from the underlying tissue during insertion of the separation member therebetween, wherein the bottom surface is generally smooth so that the underlying tissue is not damaged and the top surface is generally smooth so that the dura membrane is not damaged during insertion of the separation member between the dura membrane and the underlying tissue; and
    a cutting element that includes a single fixed lower blade with a cutting edge and a single movable upper blade with a cutting edge that cooperate to dissect the elevated membrane, wherein the lower blade has a bottom surface that is generally smooth and a top edge that forms the lower blade cutting edge, wherein the fixed lower blade is positioned within the cutout of the separation member footplate, wherein the height of the footplate is generally greater than or equal to the height of the lower blade, wherein the lower blade bottom surface is positioned not below the bottom surface of the footplate and the lower blade top cutting edge is position below the top surface of the footplate, wherein the fixed lower blade is a separate element not defined by the separation member footplate, and wherein the cutout extends vertically all the way through the separation member footplate and, because the separation member is a separate element from the lower blade, a gap is formed between the footplate outer rim and the lower blade at a leading edge of and at both sides of the lower blade, wherein during insertion between the dura membrane and the underlying tissue to separate and elevate the dura membrane from the underlying tissue, the generally smooth bottom surface of the separation member contacts and slides along the underlying tissue with the generally smooth bottom surface of the lower blade positioned not below the separation member bottom surface so that the lower blade bottom surface does not damage the underlying tissue, and the top surface of the separation member contacts and slides along the elevated dura membrane with the top cutting edge of the lower blade positioned below the separation member top surface so that the lower blade top cutting edge does not contact and damage the dura membrane, wherein the separation member separates and protects the dura membrane and the underlying tissue from damage by the lower blade.

2. The surgical apparatus of claim 1, wherein the fixed lower blade is coupled to the separation member.

3. The surgical apparatus of claim 1, wherein the separation member includes a tip that is rounded so that the tip inserts between but does not damage the underlying tissue or the derma membrane upon insertion therebetween.

4. The surgical system of claim 1, wherein the footplate is generally oval and the cutout is generally oval.

5. A surgical apparatus for separating a dura membrane from underlying tissue and dissecting the dura membrane, comprising:
  a cutting element including a single generally vertical fixed lower blade with a cutting edge and a single generally vertical movable upper blade with a cutting edge, wherein the lower blade has a bottom surface that is generally smooth and a top edge that forms the lower blade cutting edge;
  a separation member that comprises a footplate in the form of an outer rim defining in internal cutout and a top surface and a bottom surface that together define a height that separates and elevates the dura membrane from the underlying tissue during insertion of the separation member between the dura membrane and the underlying tissue, wherein the height of the footplate is generally greater than the height of the lower blade, wherein the lower blade is positioned within the footplate cutout with the bottom surface of the lower blade not below the bottom surface of the footplate and with the top cutting edge of the lower blade below the top surface of the footplate, wherein the fixed lower blade is a separate element not defined by the separation member footplate, and wherein the bottom surface is generally smooth so that the underlying tissue is not damaged and the top surface is generally smooth so that the dura membrane is not damaged during insertion of the separation member between the dura membrane and the underlying tissue;
  a stationary post coupled to the separation member, the fixed lower blade of the cutting element coupled to the stationary post, the separation member, or both;
  a mobile post mechanically linked to the movable upper blade of the cutting element;
  a first handle coupled to the stationary post; and
  a second handle mechanically linked to the mobile post;
  wherein during insertion between the dura membrane and the underlying tissue to separate and elevate the dura membrane from the underlying tissue, the generally smooth bottom surface of the separation member contacts and slides along the underlying tissue with the generally smooth bottom surface of the lower blade positioned not below the separation member bottom surface so that the lower blade bottom surface does not damage the underlying tissue, and the top surface of the separation member contacts and slides along the elevated dura membrane with the top cutting edge of the lower blade positioned below the separation member top surface so that the lower blade top cutting edge does not contact and damage the dura membrane, wherein the separation member separates and protects the dura membrane and the underlying tissue from damage by the lower blade, and
  wherein manipulation of the second handle relative to the first handle operates the cutting element to move the upper blade cutting edge into shearing engagement with the lower blade cutting edge to dissect the elevated dura membrane.

6. The surgical system of claim 5, wherein the fixed lower blade is coupled to and extends from the separation member, the stationary post, or both.

7. The surgical system of claim 5, wherein the separation member includes a tip that is rounded so that the tip inserts between but does not damage the underlying tissue or the derma membrane upon insertion therebetween.

8. The surgical system of claim 5, wherein the separation member is rigidly coupled to the stationary post.

9. The surgical apparatus of claim 5, wherein the cutout extends vertically all the way through the separation member footplate and, because the separation member is a separate element from the lower blade, a gap is formed between the footplate outer rim and the lower blade at a leading edge of and at both sides of the lower blade.

10. The surgical apparatus of claim 5, wherein the footplate is generally oval and the cutout is generally oval.

11. A surgical apparatus for separating a dura membrane from underlying tissue and dissecting the dura membrane, comprising:
  a cutting element including a single fixed lower blade with a cutting edge and a single movable upper blade with a cutting edge;
  a separation member in operable communication with the cutting element, wherein the separation member comprises a footplate in the form of an outer rim defining in internal cutout and top and bottom surfaces that define a height that separates and elevates the dura membrane from the underlying tissue during insertion of the separation member between the dura membrane and the underlying tissue, wherein the cutout extends vertically all the way through the separation member footplate, wherein the height of the footplate is greater than the height of the lower blade, wherein the lower blade is positioned within the footplate cutout with the bottom surface of the lower blade not below a bottom surface of the footplate and with the top surface of the lower blade below a top surface of the footplate, wherein the bottom surface of the footplate is generally flat and generally smooth so that the underlying tissue is not damaged during insertion of the separation member between the dura membrane and the underlying tissue, wherein the fixed lower blade is a separate element not defined by the separation member footplate, and wherein the separation member includes a tip that is rounded so that the tip inserts between but does not damage the underlying tissue or the derma membrane upon insertion therebetween;
a stationary post coupled to the separation member, the fixed lower blade of the cutting element coupled to the stationary post, the separation member, or both;
a mobile post mechanically linked to the movable upper blade of the cutting element;
a first handle coupled to the stationary post; and
a second handle mechanically linked to the mobile post;
wherein during insertion between the dura membrane and the underlying issue to separate and elevate the dura membrane from the underlying tissue, the generally smooth bottom surface of the separation member contacts and slides along the underlying tissue with the generally smooth bottom surface of the lower blade positioned not below the separation member bottom surface so that the lower blade bottom surface does not damage the underlying tissue, and the top surface of the separation member contacts and slides along the elevated dura membrane with the top cutting edge of the lower blade positioned below the separation member top surface so that the lower blade top cutting edge does not contact and damage the dura membrane, wherein the separation member separates and protects the dura membrane and the underlying tissue from damage by the lower blade, and
wherein manipulation of the second handle relative to the first handle operates the cutting element to move the upper blade cutting edge into shearing engagement with the lower blade cutting edge to dissect the elevated dura membrane.

12. The surgical apparatus of claim 11, wherein the footplate is generally oval and the cutout is generally oval.

* * * * *